United States Patent
Schubert et al.

(10) Patent No.: US 6,894,610 B2
(45) Date of Patent: May 17, 2005

(54) MONITORING AND WARNING SYSTEM FOR INDIVIDUALS WORKING UNDER HAZARDOUS OPERATING CONDITIONS

(75) Inventors: Axel Schubert, Berlin (DE); Dieter Lubkoll, Berlin (DE)

(73) Assignee: MSA Auer GmbH, Berlin (DE)

( * ) Notice: Subject to any disclaimer, the term of this patent is extended or adjusted under 35 U.S.C. 154(b) by 92 days.

(21) Appl. No.: 10/381,447
(22) PCT Filed: Feb. 20, 2002
(86) PCT No.: PCT/DE02/00655
§ 371 (c)(1), (2), (4) Date: Apr. 23, 2003
(87) PCT Pub. No.: WO02/086834
PCT Pub. Date: Oct. 31, 2002

(65) Prior Publication Data
US 2004/0135693 A1 Jul. 15, 2004

(30) Foreign Application Priority Data
Apr. 24, 2001 (DE) ......... 101 20 775

(51) Int. Cl.⁷ ............................. H04Q 1/30
(52) U.S. Cl. ......... 340/531; 340/539.1; 340/539.13; 340/539.22; 340/539.24; 340/286.02; 700/3
(58) Field of Search .............. 340/531, 539.1, 340/539.11, 539.13, 539.22, 539.24, 539.26, 286.02, 286.05; 700/3

(56) References Cited

U.S. PATENT DOCUMENTS

| | | | |
|---|---|---|---|
| 5,899,204 A | 5/1999 | Cochran | 128/205.23 |
| 5,990,793 A * | 11/1999 | Bieback | 340/573.1 |
| 6,198,394 B1 * | 3/2001 | Jacobsen et al. | 340/573.1 |
| 6,472,988 B1 | 10/2002 | Feld et al. | 340/573.1 |

FOREIGN PATENT DOCUMENTS

DE  198 22 412 A1  11/1999  ........ A62B/27/00

* cited by examiner

*Primary Examiner*—Daryl C. Pope
(74) *Attorney, Agent, or Firm*—Welsh & Katz, Ltd.

(57) ABSTRACT

A monitoring and warning system for firefighters and other people exposed to similar hazards includes mutiple monitoring, warning and control devices (1, 9 through 16) and a telemetric module (17) for transmitting information data to a base station and for receiving commands. All units of the system are connected seperately to a common—open-type or closed-type—bus (8) and configured either for master-slave or for master-master operation. The system operates on simple and efficient connections, more units can be added easily, it is fast and faultless and can also be used in areas subject to explosion hazards.

5 Claims, 1 Drawing Sheet

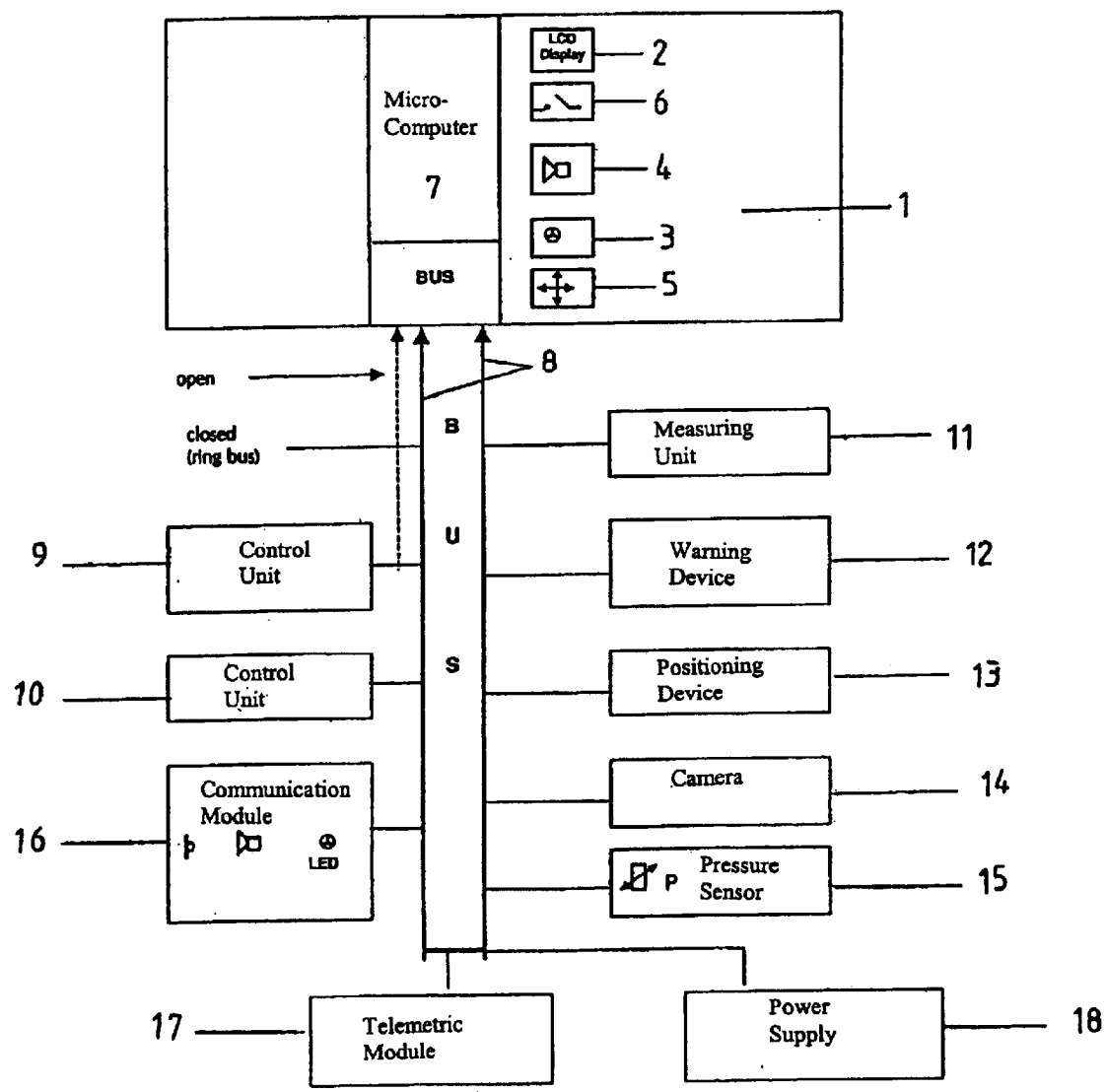

MONITORING AND WARNING SYSTEM FOR INDIVIDUALS WORKING UNDER HAZARDOUS OPERATING CONDITIONS

FIELD OF THE INVENTION

This invention relates to a monitoring and warning system for people working in hazardous environments, preferably comprising a monitoring device (ICU) that consists of a microcomputer as well as data and alarm displays and alarm sensors and is connected to a compressed air breathing apparatus, a telemetric module and other monitoring and/or control units.

BACKGROUND OF THE INVENTION

Operations in mining and tunnel construction, some industrial branches, the military as well as fire-fighting or rescue missions in areas contaminated by natural disasters or accidents present considerable hazards to the respective workers. Such hazards can be toxic and/or explosive gases, hazardous radiation or high temperatures. Rescue workers are equally exposed to hazards created by falling objects and exposure to other physical impacts or extreme physical strain. In addition, the time people can work when breathing from a compressed air breathing apparatus is limited to the capacity of the compressed air bottle and must not be exceeded.

Various interconnected electronic warning, monitoring, control and information devices (hereinafter called 'units' for short) are required to monitor operating conditions, gather site information, check vital functions, determine the position and alert the respective person in hazardous or even life-threatening conditions or to control and monitor specific apparatuses such as a pressure reducer connected to a compressed air breathing apparatus or an oxygen system. For example, a monitoring and warning system consisting of the following units is provided for fire fighters wearing compressed air breathing apparatuses:

- a monitoring device (ICU) for the compressed air breathing apparatus mainly containing pressure, motion, and temperature sensors, alarm and data displays (LED and LCD) as well as acoustic alarms;
- a gas warning device for toxic and/or explosive gases
- a positioning device (such as GPS)
- a pressure gauge for measuring and monitoring compressed air bottles
- control devices for the pressure reducer and the oxygen system
- a measuring instrument for monitoring vital functions, and
- a camera/thermal imaging camera information system.

A telemetric module is another important unit of the system that is used to transmit system status and individual unit data to the base stations outside the immediate operating area to allow outside control over the people in the operating area. In addition, commands, information and messages from the base station are to be forwarded from the base station to the respective person via specific units.

Such complex electronic safety systems have considerable requirements regarding communication among the units and with the telemetric module as well as incorporating new components. Furthermore, compliance with applicable national or regional standards/regulations is required. Expensive additional measures have to be taken for an explosion-protected and trouble-free design and for integrating each unit.

It is therefore the problem of the invention to design a monitoring and warning system equipped with a telemetric module for bidirectional communication with a base station in such a way that simple and fail-safe connection setup, easy integration of additional units, and fast data transfer among system components and to the base station are ensured.

SUMMARY OF THE INVENTION

The inventive idea is that, in a device system worn by a person exposed to a hazard, all monitoring and alarm units, control units and the telemetric module are integrated in a common bus of open or closed design wherein the units are either switched for master-slave or for master-master operation. In master-slave operation, one of the units receives or controls the information of the other units in the system and forwards it to the telemetric module. In master-master operation with peer units, the units can exchange data among each other, and each unit can send its data directly to the telemetric module.

A system configured in this way requires less wiring and interconnecting. Additional units can easily be incorporated into the bus system. The status and data of each unit are transferred in parallel to a remote base station, which allows fast transfer. At the same time, messages and commands from the base station can be transferred to the units. The units can be coupled to the bus in such a way that the requirements of explosion protection and faultless operation of the monitoring and warning system are met. On the other hand, the bus link can be configured in such a way that information can be transferred in the opposite direction in the event of disconnected line or that the risk of a disconnected line is eliminated.

The subclaims and the description of a preferred embodiment of the invention below disclose other characteristics and useful improvements of the invention or other advantages.

For example, the bus can either be configured for parallel and fast transfer of data, address and control signals or for serial information transfer to reduce wiring.

According to another characteristic of the invention, each unit is connected to the bus by isolated connections and has its own power supply. This proposed solution is useful for monitoring and warning systems that are to be used in areas subject to explosion hazards.

A central power supply can be directly integrated in the bus if the system is used in areas not subject to explosion hazards.

A useful improvement of the invention is a star-shaped arrangement of the units where one unit has the master function, scans the data from the other units and transfers it to the telemetric module; another improvement is connecting the units in parallel to the bus, which reduces cabling. According to a preferred embodiment with improved safety standards, a serial ring bus is provided and all information from all units is transferred serially while data can be transferred in the opposite direction if the bus is disconnected. Yet another conceivable improvement of the invention is a high-frequency connection via which data can be exchanged among the units without connecting cables and the risk of a disconnected line is eliminated. The HF connection also allows master-slave or master-master operation.

CONCISE DESCRIPTION OF THE DRAWINGS

The FIGURE is a block diagram of the monitoring and warning system of the subject invention.

An embodiment of the invention is explained in greater detail below with reference to the FIGURES. One single FIGURE shows a block diagram of a monitoring and warning system connected to a compressed air breathing apparatus (not shown) whose units are interconnected via a ring bus. The dashed lines in the FIGURE indicate that the bus may also have an open design.

The FIGURE shows a central monitoring unit 1 named ICU that is connected to a compressed air breathing apparatus and comprises a data display (LCD) 2, an alarm display (LED) 3, an acoustic alarm 4, a motion detector 5 and function keys 6 and a microcomputer ($\mu$C) 7. In addition to the monitoring device 1, a first control unit 9 for an electronic pressure reducer of the compressed air breathing apparatus (not shown), a second control unit 10 for an oxygen system (not shown), a measuring unit 11 for monitoring the respective person's vital functions, a gas warning device 12 for detecting explosive and/or toxic gases, a positioning device 13 with a camera 14, a pressure sensor 15 for determining the pressure in the compressed air bottle, a helmet/mask communication module 16 for data display in the wearer's immediate field of vision using a head-up display, and a telemetric module 17 for transferring the data from each unit to a central base station (not shown) or for receiving commands and messages from the base station to the units or the wearer are connected to a closed-type ring bus 8. In addition, a central power supply 18 can optionally be connected to the ring bus 8 to supply power as required to all units of the monitoring and warning system. This power supply is not provided when the units are connected separately to the ring bus 8 and have their own power supplies so that the system is suitable for use in areas subject to explosion hazards. Other units can easily integrated into such a monitoring and warning system interconnected via a bus 8.

Each unit fulfills its respective functions within the overall system and passes the respective information on to the controlling devices, the alarm and data displays, the alarm sensors in the monitoring device (ICU) 1 or in the helmet/mask communication module 16 and—depending on mode of operation—either directly or via a master unit (such as the ICU 1) to the telemetric module 17 to transfer the information from the monitoring and warning devices in parallel to the base station.

The system is not shut down even when the bus line is disconnected when the units are connected as shown via a ring bus 8 because the information can also be transferred in the opposite direction.

The FIGURE uses the '?' symbol to refer to a HF model for communication without a bus link (HF bus) where the power supply does not need an HF module as it is connected to at least one unit whose information is known to the power supply.

List of Reference Symbols

1 Monitoring device (ICU)
2 Data display (LCD) of 1
3 Alarm display (LED) of 1
4 Acoustic alarm of 1
5 Motion detector of 1
6 Function keys of 1
7 Microprocessor ($\mu$C) of 1
8 Bus (ring bus)
9 First control unit (for pressure reducer)
10 Second control unit (for oxygen system)
11 Measuring unit (vital functions)
12 Gas warning device (explosive and toxic gases)
13 Positioning device (PSB)
14 Camera
15 Pressure sensor (compressed air bottle pressure)
16 Helmet/mask communication module/head-up display
17 Telemetric module
18 Power supply

What is claimed is:

1. A monitoring and warning system for a person working in hazardous environments, comprising a monitoring device connected to a compressed air breathing apparatus with a microcomputer, data and alarm displays, alarm sensors, motion sensors, and a telemetric module hi-directionally connected with a base station, and having a closed bus system or an open bus system secured to the person, to which the monitoring device and the telemetric module and a plurality of additional monitoring, communication and control units are connected selectively and exchangeably, galvanically with a central power supply or galvanically isolated with a separate power supply via optocouplers, fiber optics or a high frequency radio connection.

2. The monitoring and warning system according to claim 1 characterized in that it comprises a bus with parallel transfer of data, address and control signals.

3. The monitoring and warning system according to claim 1 characterized in that it comprises a serial bus for serial transfer of data, address and control signals over a single line section.

4. The monitoring and warning system according to claim 1 characterized in that the units are connected in a star shape wherein one of the units operates as bus master for scanning the respective data from the other units and transferring this data to the telemetric module.

5. The monitoring and warning system according to claim 1 characterized in that the units of the system are connected in series to a ring bus.

\* \* \* \* \*